(12) United States Patent
Fuchigami et al.

(10) Patent No.: US 10,506,997 B2
(45) Date of Patent: Dec. 17, 2019

(54) X-RAY DIAGNOSTIC APPARATUS

(71) Applicant: TOSHIBA MEDICAL SYSTEMS CORPORATION, Otawara-Shi (JP)

(72) Inventors: Ko Fuchigami, Otawara (JP); Jun Sakakibara, Otawara (JP); Yuichiro Watanabe, Yaita (JP); Yusuke Kanno, Otawara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 451 days.

(21) Appl. No.: 14/833,475

(22) Filed: Aug. 24, 2015

(65) Prior Publication Data
US 2015/0359497 A1 Dec. 17, 2015

Related U.S. Application Data

(63) Continuation of application No. PCT/JP2014/054197, filed on Feb. 21, 2014.

(30) Foreign Application Priority Data

Mar. 1, 2013 (JP) .................................. 2013-040843

(51) Int. Cl.
*A61B 6/00* (2006.01)
*A61B 6/04* (2006.01)

(52) U.S. Cl.
CPC ............ *A61B 6/467* (2013.01); *A61B 6/0407* (2013.01); *A61B 6/0457* (2013.01); *A61B 6/487* (2013.01); *A61B 6/548* (2013.01)

(58) Field of Classification Search
None
See application file for complete search history.

(56) References Cited

U.S. PATENT DOCUMENTS

2002/0041654 A1* 4/2002 Hayashi ............... A61B 6/4441
378/196
2002/0090058 A1* 7/2002 Yasuda .................... A61B 6/08
378/205

(Continued)

FOREIGN PATENT DOCUMENTS

JP 08-130752 A 5/1996
JP 2002-251235 A 9/2002

(Continued)

OTHER PUBLICATIONS

International Search Report dated Apr. 8, 2014 in PCT/JP2014/054197 filed Feb. 21, 2014 with English translation.

(Continued)

*Primary Examiner* — Hoon K Song
(74) *Attorney, Agent, or Firm* — Oblon, McClelland, Maier & Neustadt, L.L.P.

(57) ABSTRACT

An X-ray diagnostic apparatus includes a display, a holding device, bed device, a gesture detecting device and a processing circuitry. The holding device includes an X-ray irradiator, an X-ray detector, and a supporter that supports the X-ray irradiator and the X-ray detector. The bed device is available to place an object on. The gesture detecting device recognizes a gesture of a person. The processing circuitry identifies a state of the X-ray diagnostic apparatus based on at least one of the display, the X-ray irradiator, the X-ray detector, the holding device and the bed device, determines an operation detail based on a combination of the identified state and the recognized gesture, and operates at least one of the display, the holding device, the bed device, a speaker and a room light according to the determined operation detail.

15 Claims, 5 Drawing Sheets

(56) References Cited

U.S. PATENT DOCUMENTS

| | | | | |
|---|---|---|---|---|
| 2004/0125920 A1* | 7/2004 | Zaiki | ................ | A61B 6/0457 |
| | | | | 378/195 |
| 2008/0253519 A1* | 10/2008 | Bonfiglio | ............ | A61B 6/00 |
| | | | | 378/65 |
| 2015/0253865 A1* | 9/2015 | Hayashi | ............ | A61B 6/467 |
| | | | | 600/436 |

FOREIGN PATENT DOCUMENTS

| | | |
|---|---|---|
| JP | 2008-132033 A | 6/2008 |
| JP | 2008-529707 A | 8/2008 |
| JP | 2011-186730 A | 9/2011 |
| JP | 2011-192081 A | 9/2011 |
| WO | WO 2006/087689 A2 | 8/2006 |

OTHER PUBLICATIONS

International Preliminary Report on Patentability and Written Opinion dated Sep. 1, 2015 in PCT/JP2014/054197 (submitting English translation only).

* cited by examiner

| | STEPS | GESTURES | OPERATION DETAILS | TIME SHOWN IN FIG. 4 |
|---|---|---|---|---|
| DURING DEVICE-OPERATION | DURING HOLDING DEVICE-OPERATION | LEFT, RIGHT, UPWARD OR DOWNWARD MOVEMENT | STOPPING OPERATION OF HOLDING DEVICE | T1, T2 |
| | DURING BED DEVICE-OPERATION | LEFT, RIGHT, UPWARD OR DOWNWARD MOVEMENT | STOPPING OPERATION OF BED DEVICE | T1, T2 |
| DURING IMAGING | DURING SIMPLE FLUOROSCOPY IMAGING-OPERATION | LEFT OR RIGHT MOVEMENT | TURNING ON/OFF RM-OPERATION | |
| | | UPWARD OR DOWNWARD MOVEMENT | CHANGING IMAGING PROGRAM (TO NEXT/PREVIOUS ONE) | T3 |
| | DURING LIH-DISPLAY | LEFT OR RIGHT MOVEMENT | CHANGING BRIGHTNESS (UP/DOWN) | T3 |
| | | UPWARD OR DOWNWARD MOVEMENT | CHANGING CONTRAST (UP/DOWN) | |
| | DURING RM-OPERATION | LEFT OR RIGHT MOVEMENT | CHANGING SUPERPOSITION COEFFICIENT (UP/DOWN) | T3 |
| | | UPWARD OR DOWNWARD MOVEMENT | CHANGING TO FLUOROSCOPIC SUBTRACTION OR RM-OPERATING | |
| DURING REPRODUCTION | DURING MOVING IMAGE-REPRODUCTION | LEFT OR RIGHT MOVEMENT | CHANGING REPRODUCTION SPEED (UP/DOWN) | T4 |
| | | UPWARD OR DOWNWARD MOVEMENT | CUTTING FEEDING (FORWARD/BACKWARD) | |
| | DURING MAP IMAGE-DISPLAY | LEFT OR RIGHT MOVEMENT | EXECUTING AUTOMATIC ANGLE FUNCTION | T4 |
| | | UPWARD OR DOWNWARD MOVEMENT | EXECUTING ORIGINAL IMAGE DISPLAY FUNCTION | |
| | DURING STILL IMAGE-DISPLAY | LEFT OR RIGHT MOVEMENT | PANNING | T4 |
| | | UPWARD OR DOWNWARD MOVEMENT | CUTTING FEEDING (FORWARD/BACKWARD) | |
| | DURING DSA IMAGE-DISPLAY | LEFT, RIGHT, UPWARD OR DOWNWARD MOVEMENT | PIXEL SHIFTING (LEFT/RIGHT/UPWARD/DOWNWARD) | T4 |
| DURING STANDBY | | LEFT OR RIGHT MOVEMENT | CHANGING VOLUME (UP/DOWN) | T5 |
| | | UPWARD OR DOWNWARD MOVEMENT | TURNING ON/OFF SPEAKER | |

FIG. 5

X-RAY DIAGNOSTIC APPARATUS

CROSS-REFERENCE TO RELATED APPLICATION

This application is a Continuation Application of No. PCT/JP2014/54197, filed on Feb. 21, 2014, and the PCT application is based upon and claims the benefit of priority from Japanese Patent Application No. 2013-40843, filed on Mar. 1, 2013, the entire contents of which are incorporated herein by reference.

FIELD

An embodiment as an aspect of the present invention relates to an X-ray diagnostic apparatus for an imaging.

BACKGROUND

Conventionally, in an industrial field including nondestructive inspection, and a medical field including medical examination, an X-ray diagnostic apparatus has been widely used that irradiates a test target or an object with radiation (typically, X-rays), detects the distribution of intensities of radiation having passed through the test target or the object, and obtains an image of the test target or the object.

Furthermore, an image processing apparatus is disclosed that allows application programs running in background to be operated. This apparatus displays an image of a web browser on a display, which is an application program running in foreground, in a normal mode. In background, a music player, which is another application program, is running. When a user manually inputs a gesture, the gesture is taken by a video camera, a gesture command is recognized on the basis of the movement of the gesture, and the operation of the music player is controlled accordingly. The movement of a hand is displayed as a trajectory. The jacket photographs of pieces of music to be played by the music player are moved and displayed by gestures, such as a left flick and a right flick. Input of a hand holding gesture controls reproduction and stop of the piece of music.

During cardiac catheter manipulation, a manipulator, such as a medical doctor, cannot directly touch the X-ray diagnostic apparatus (input device etc.) with the hands in order to keep the hands clean. Consequently, for an operation, the manipulator indirectly operates the device by verbally instructing an operator, such as an assistant or a technician. It is, however, difficult to verbally convey intended operation details correctly. For some operations, the description is required to be made specifically in detail. Consequently, the operation intended by the manipulator cannot be easily achieved.

For example, when the assistant or the like is verbally instructed to stop a holding device (a device for holding a C-arm and the like) currently in operation, a time difference occurs between the timing of a stop instruction at a position intended by the manipulator and the timing of a stop operation actually performed by the assistant or the like according to the instruction. Consequently, time and efforts are required for an operation of matching the position intended by the manipulator with the actual position of the holding device.

Furthermore, there is a possibility that the time and effort required for the operation of the X-ray diagnostic apparatus cause the object to be exposed to unnecessary radiation exposure owing to inefficient treatment.

A motion sensor and the X-ray diagnostic apparatus may be combined to allow a screen operation for the X-ray diagnostic apparatus to be performed by a gesture. Unfortunately, there are problems in that the operation is only for the currently displayed screen, and the types of recognizable gestures are limited, thus allowing only a small number of executable operations.

BRIEF DESCRIPTION OF THE DRAWINGS

In accompanying drawings,

FIG. 5 is a diagram showing an example of operation details by the combination of the step included in the manipulation and the gesture in the X-ray diagnostic apparatus according to the present embodiment.

DETAILED DESCRIPTION

An X-ray diagnostic apparatus according to a present embodiment is described with reference to the accompanying diagrams.

To solve the above-described problems, the present embodiment provides the X-ray diagnostic apparatus, including: a display; a holding device including an X-ray irradiator, an X-ray detector, and a supporter that supports the X-ray irradiator and the X-ray detector; a bed device available to place an object on; a gesture detecting device configured to recognize a gesture of a person; and a processing circuitry configured to identify a state of the X-ray diagnostic apparatus based on at least one of the display, the X-ray irradiator, the X-ray detector, the holding device and the bed device, to determine an operation detail based on a combination of the identified state and the recognized gesture, and to operate at least one of the display, the holding device, the bed device, a speaker and a room light according to the determined operation detail.

The X-ray diagnostic apparatus according to the present embodiment can identify a state of the X-ray diagnostic apparatus, and determine the operation detail on the basis of the combination of a gesture by a manipulator such as a doctor, and the state of the X-ray diagnostic apparatus. Consequently, the treatment efficiency can be improved. Furthermore, unnecessary radiation exposure of an object due to inefficient treatment can be reduced.

Figure 1:
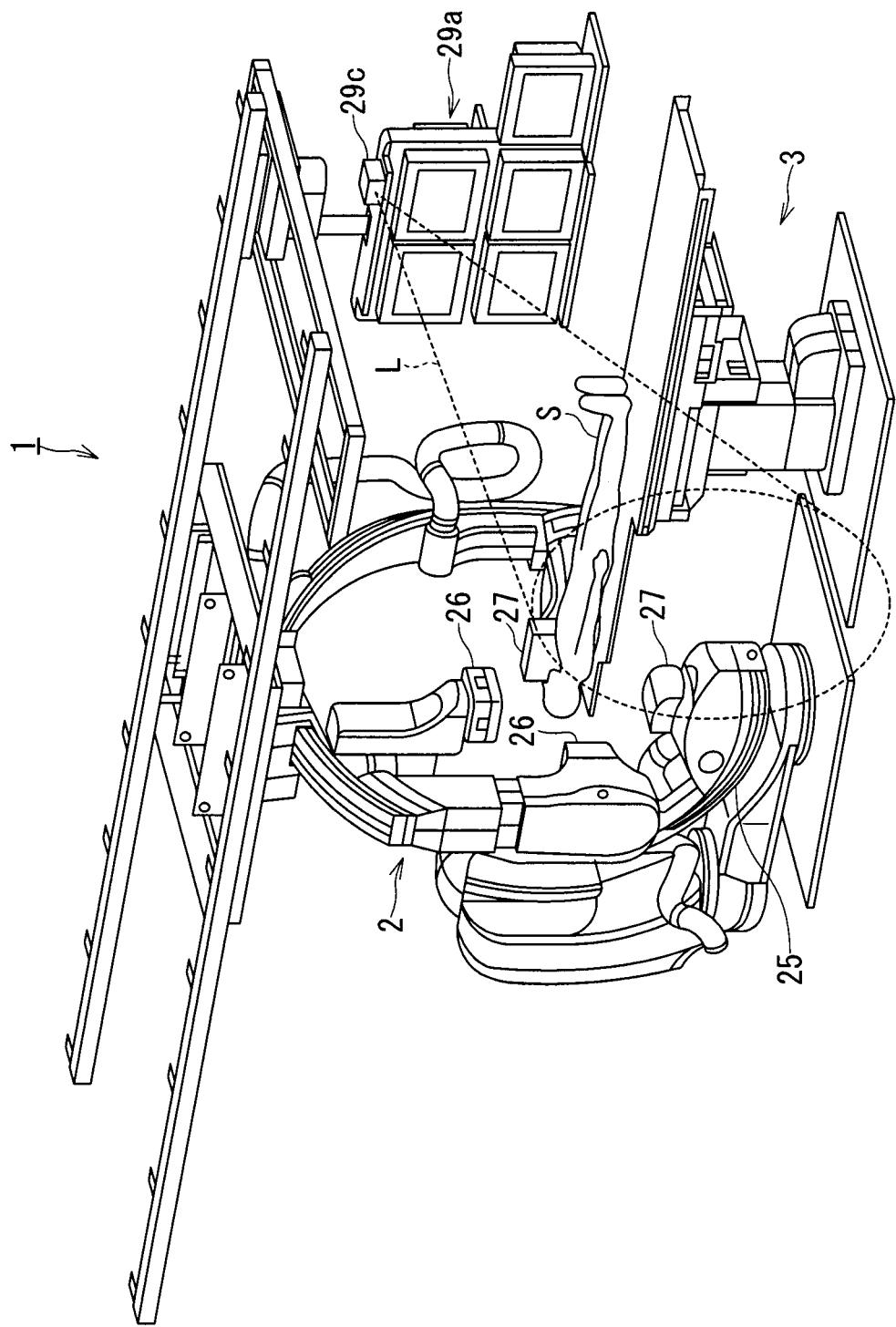
FIG. 1 is a schematic diagram showing a structure of an appearance of an X-ray diagnostic apparatus according to a present embodiment.
Figure 2:
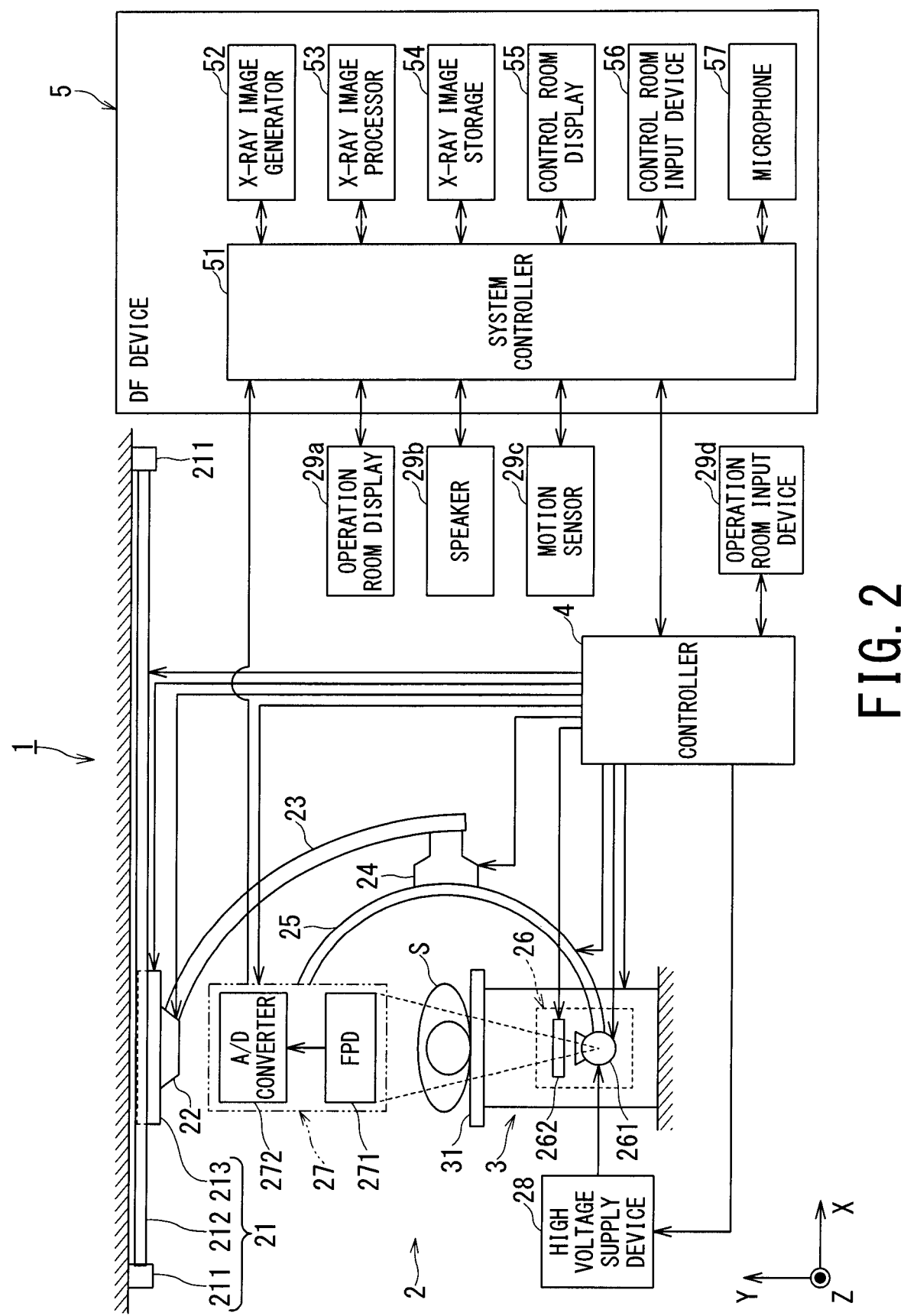
FIG. 2 is a schematic diagram showing a configuration of the X-ray diagnostic apparatus according to the present embodiment.

FIG. 1 is a schematic diagram showing a structure of an appearance of the X-ray diagnostic apparatus according to the present embodiment. FIG. 2 is a schematic diagram showing a configuration of the X-ray diagnostic apparatus according to the present embodiment.

FIG. 1 shows the X-ray diagnostic apparatus 1 that includes a ceiling-traveling Q-arm, and a floor-traveling C-arm. FIG. 2 shows an X-ray diagnostic apparatus 1 that only includes a ceiling-traveling C-arm (under-tube type). The description is hereinafter made with reference to the X-ray diagnostic apparatus 1 that only includes the ceiling-traveling C-arm as shown in FIG. 2. The X-ray diagnostic apparatus 1 mainly includes a holding device 2, a bed device 3, a controller 4, and a DF (digital fluoroscopy) device 5. The holding device 2, the bed device 3, and the controller 4 are typically installed in a surgical operation room (test and treatment room), while the DF device 5 is installed in a control room adjoining to the surgical operation room. The X-ray diagnostic apparatus according to the present invention is not limited to the X-ray diagnostic apparatus 1 that includes the ceiling-traveling Q-arm and the floor-traveling C-arm shown in FIG. 1, and the apparatus that only includes the ceiling-traveling C-arm shown in FIG. 2. Alternatively, an X-ray diagnostic apparatus that only includes a ceiling-traveling Ω-arm or a floor-traveling C-arm may be adopted. The X-ray diagnostic apparatus according to the present invention may be an X-ray diagnostic apparatus that includes an over-tube C-arm.

The holding device 2 includes a sliding mechanism 21, a perpendicular axis turning mechanism 22, a suspension arm 23, a C-arm turning mechanism 24, a C-arm 25, an X-ray irradiator 26, an X-ray detector 27, and a high voltage supply device 28.

The sliding mechanism 21 includes, a Z-axis direction rail 211, an X-axis direction rail 212, and a vehicle 213. The sliding mechanism 21 is controlled by the controller 4 to slide the perpendicular axis turning mechanism 22, the suspension arm 23, the C-arm turning mechanism 24, the C-arm 25, the X-ray irradiator 26, and the X-ray detector 27 integrally in the horizontal direction.

The Z-axis direction rail 211 is arranged longitudinally in a Z-axis direction (the longitudinal axis direction of a top table 31), and held on the ceiling.

The X-axis direction rail 212 is arranged in an X-axis direction (the short axis direction of the top table 31), and held by the Z-axis direction rail 211 via rollers (not shown) at the opposite ends. The X-axis direction rail 212 is controlled by the controller 4 to move on the Z-axis direction rail 211 in the Z-axis direction.

The vehicle 213 is supported on the X-axis direction rail 212 via rollers (not shown). The vehicle 213 is controlled by the controller 4 to move on the X-axis direction rail 212 in the X-axis direction.

The X-axis direction rail 212 that supports the vehicle 213 is movable on the Z-axis direction rail 211 in the Z-axis direction. The vehicle 213 is movable on the X-axis direction rail 212 in the X-axis direction. Consequently, the vehicle 213 is movable in the horizontal direction (the X-axis direction and the Z-axis direction) in the surgical operation room.

The perpendicular axis turning mechanism 22 is turnably supported by the vehicle 213. The perpendicular axis turning mechanism 22 is controlled by the controller 4 to turn the suspension arm 23, the C-arm turning mechanism 24, the C-arm 25, the X-ray irradiator 26, and the X-ray detector 27 integrally in the perpendicular axis turning direction.

The suspension arm 23 is supported by the perpendicular axis turning mechanism 22.

The C-arm turning mechanism 24 is turnably supported by the suspension arm 23. The C-arm turning mechanism 24 is controlled by the controller 4 to turn the C-arm 25, the X-ray irradiator 26, and the X-ray detector 27 integrally in the turning direction with respect to the suspension arm 23.

The C-arm 25 is supported by the C-arm turning mechanism 24, and arranges the X-ray irradiator 26 and the X-ray detector 27 at the opposite positions centered at an object S. A rail (not shown) is provided on the back or a side of the C-arm 25. Through the rail sandwiched by the C-arm turning mechanism 24 and the C-arm 25, the C-arm 25 is controlled by the controller 4 to move the X-ray irradiator 26 and the X-ray detector 27 in an arc direction of the C-arm 25 along an arc locus.

The X-ray irradiator 26 is provided at one end of the C-arm 25. The X-ray irradiator 26 is provided movable to-and-fro according to control by the controller 4. The X-ray irradiator 26 includes an X-ray tube (X-ray source) 261 and a movable diaphragm device 262.

The X-ray tube 261 is supplied by the high voltage supply device 28 with high voltage power, and generates X-rays according to the condition of the high voltage power.

The movable diaphragm device 262 supports aperture blades made of material for blocking X-rays, in a manner movable at an X-ray irradiation port of the X-ray tube 261 under control of the controller 4. A radiation quality adjusting filter (not shown) that adjusts the quality of X-ray radiation emitted from the X-ray tube 261 may be provided on the front surface of the X-ray tube 261.

The X-ray detector 27 is provided at the other end of the C-arm 25 to face the X-ray irradiator 26. The X-ray detector 27 is provided movable to-and-fro under control by the controller 4. The X-ray detector 27 includes an FPD (flat panel detector) 271 and an A/D (analog to digital) converter 272.

The FPD 271 includes two-dimensionally arranged detection elements. Scanning lines and signal lines are arranged orthogonal to each other between the detection elements of the FPD 271. A grid (not shown) may be provided on the front surface of the FPD 271. The grid includes grid plates made of lead or the like that absorbs X-rays well, and aluminum wood or the like which is transmittable, in an alternately stacked arrangement, in order to absorb scattered radiation incident on the FPD 271 and improve the contrast of an X-ray image.

The A/D converter 272 converts projection data that is a time-series analog signal (video signal) and output from the FPD 271, into a digital signal, and outputs the signal to the DF device 5.

The X-ray detector 27 may be an I. I. (image intensifier)-TV system. The I. I.-TV system converts X-rays passing through the object S and directly incident X-rays into visible light, increases the luminance through a process of light-electron-light conversion, forms projection data with high sensitivity, and converts optical projection data into an electric signal using a CCD (charge coupled device) image pickup element.

The high voltage supply device 28 can supply the X-ray tube 261 of the X-ray irradiator 26 with high voltage power according to control by the controller 4.

The X-ray diagnostic apparatus 1 includes an operation room display 29a, a speaker 29b, a gesture detector (motion sensor) 29c, and an operation room input device 29d, in the surgical operation room. The operation room display 29a displays an image together with text information with various parameters, calibration markings and the like. The operation room display 29a may be a display device, such as a liquid crystal display unit.

The speaker 29b is a device that converts an electric signal from a microphone 57, which will be described later, into physical vibrations, and produces music or sound.

The motion sensor 29c is a 3D motion sensor that recognizes a gesture of a person (a manipulator, such as a medical doctor). The 3D motion sensor may internally include an RGB (red, green and blue) camera, a depth sensor, and a processor for operating dedicated software. Alternatively, the 3D motion sensor may internally include two infrared cameras, and infrared irradiation LED (light emitting diode). Through use of the motion sensor 29c, motion and the like of the manipulator in a field of view L can be detected, and the gesture of the manipulator can be recognized. The manipulator in the field of view L uses the body of himself/herself to intuitively perform a screen operation or the like for the operation room display 29a, as will be described later.

The X-ray diagnostic apparatus 1 may adopt a motion capture technique that does not need a suit with special markers and a tracker for detecting the markers, and mainly reads the motion of the person and combines the read results. Alternatively, the X-ray diagnostic apparatus 1 may adopt another motion capture technique that includes the suit with markers and the tracker.

The operation room input device 29d includes a keyboard and a mouse that can be mainly operated by the operator, such as an assistant. An input signal according to an operation is transmitted to the controller 4.

The bed device 3 is supported on the floor and, in turn, supports the top table (catheter table) 31. The bed device 3 is controlled by the controller 4 to slide (in the X- and Z-axis directions), vertically move (in the Y-axis direction) and roll the top table 31. The object S can be mounted on the top table 31. Note that the case of the holding device 2 of an under-tube type where the X-ray irradiator 26 is positioned below the top table 31 is described. Alternatively, an over-tube type where the X-ray irradiator 26 is positioned above the top table 31 may be adopted.

The controller 4 includes a processing circuitry and a memory, which are not shown. Under control by the DF device 5, the controller 4 controls driving of the sliding mechanism 21, the perpendicular axis turning mechanism 22, the C-arm turning mechanism 24, the C-arm 25, the X-ray irradiator 26 and the X-ray detector 27 of the holding device 2, and driving of the bed device 3, while controlling the operations of the X-ray irradiator 26, the X-ray detector 27 and the high voltage supply device 28 for the sake of partial imaging.

The DF device 5 has a computer-based configuration. This device performs overall control of the X-ray diagnostic apparatus 1, and image processing and the like for an X-ray image obtained by the holding device 2. The X-ray image includes at least one of a fluoroscopic image (a moving image) based on a fluoroscopic imaging, and a simple image (a still image such as a digital angiography (DA) image) based on a simple (one shot) imaging. The DF device 5 includes a system controller 51, an X-ray image generator 52, an X-ray image processor 53, an X-ray image storage 54, a control room display 55, a control room input device 56, and the microphone 57.

The system controller 51 includes a processing circuitry and a memory, which are not shown. The system controller 51 controls the controller 4 and the components 52 to 55 and 57.

The processing circuitry of the system controller 51 may be a dedicated or general-purpose CPU (central processing unit) or MPU (microprocessor unit). Alternatively, this circuit may be any of an application specific integrated circuit (ASIC), a programmable logic device and the like. The programmable logic device may be, for example, any of a simple programmable logic device (SPLD), complex programmable logic device (CPLD), field programmable gate array (FPGA) and the like. The processing circuitry reads a program stored in the memory or directly embedded in the processing circuitry, and executes the program, thereby achieving functions 61 to 66 shown in FIG. 3.

The processing circuitry may be made of a single circuit, or made of a combination of independent circuits. In the latter case, the memories for storing programs may be provided separately for the respective processing circuitries. Alternatively, a single memory may store programs corresponding to the functions of the respective circuits.

The X-ray image generator 52 is controlled by the system controller 51 to apply a logarithm conversion process (LOG process) to the projection data output from the A/D converter 272 of the holding device 2, and applies an addition process as necessary, thereby generating data on the X-ray image.

The X-ray image processor 53 is controlled by the system controller 51 to apply an image processing to the X-ray image generated by the X-ray image generator 52. The image processing may include enlarging, gradation and spatial filter processes for the data, minimum value and maximum value tracing processes for data accumulated in a time-series manner, and addition process for removing noise. The data having been subjected to the image processing by the X-ray image processor 53 is output to the operation room display 29a and the control room display 55, and stored in a storing device, such as the X-ray image storage 54.

The control room display 55 displays an image together with text information with various parameters, calibration markings and the like. As with the operation room display 29a, the control room display 55 may be a display device, such as a liquid crystal display unit.

The control room input device 56 includes a keyboard and a mouse that can be operated by the operator. An input signal according to an operation is transmitted to the system controller 51.

The microphone 57 is a device that collects ambient sound, and converts the sound into an electric signal.

Figure 3:
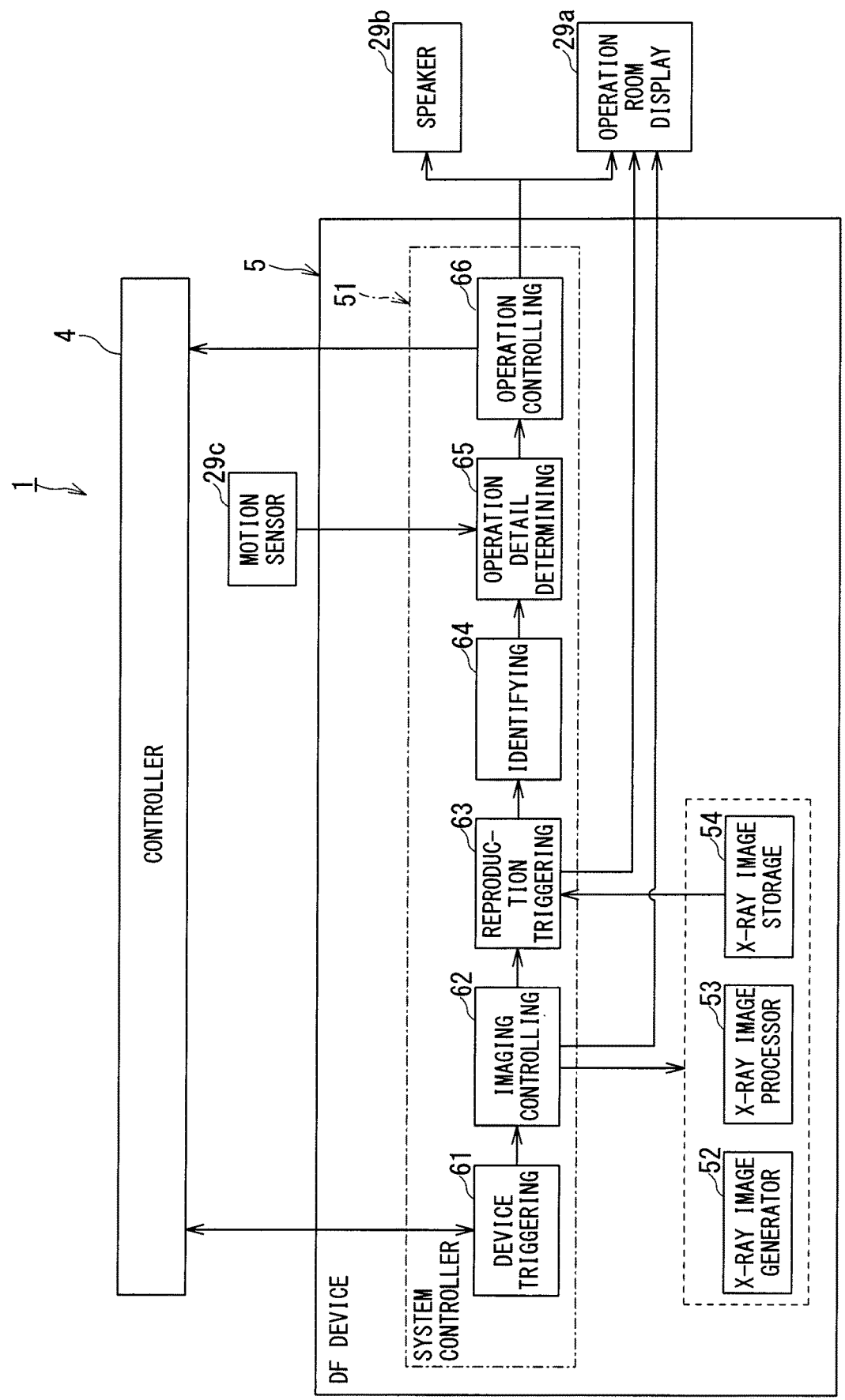
FIG. 3 is a block diagram showing functions of the X-ray diagnostic apparatus according to the present embodiment.

FIG. 3 is a block diagram showing functions of the X-ray diagnostic apparatus 1 according to the present embodiment.

The system controller 51 of the DF device 5 shown in FIG. 2 executes the program, thereby allowing the X-ray diagnostic apparatus 1 to function as a device triggering 61, an imaging controlling 62, a reproduction triggering 63, an identifying 64, an operation detail determining 65, and an operation controlling 66, as shown in FIG. 3. Some or all of the functions 61 to 66, which are the functions of the DF device 5, may be achieved in the controller 4. The functions 61 to 66, which are the functions of the X-ray diagnostic apparatus 1, may be provided as hardware in the X-ray diagnostic apparatus 1.

The device triggering 61 has the following functions. That is, after the object S is mounted on the top table 31 of the holding device 2, in order to change the X-ray irradiation position and angle, the device triggering 61 receives, via the controller 4, an instruction input from the operation room input device 29d (shown in FIG. 2), and triggers the operation of the holding device 2 and the bed device 3 shown in FIG. 2 via the controller 4 according to the instruction. For example, in order to adjust the X-ray irradiation position, the device triggering 61 starts sliding at least one of the sliding mechanism 21 of the holding device 2 and the top table 31 of the bed device 3, which are shown in FIG. 2, via the controller 4. For example, in order to adjust the X-ray irradiation angle, the device triggering 61 starts the turning operation of at least one of the perpendicular axis turning mechanism 22, the C-arm turning mechanism 24 and the C-arm 25 of the holding device 2 shown in FIG. 2, or starts the arc movement of the C-arm 25, via the controller 4.

The imaging controlling 62 has functions that receive, via the controller 4, the instruction input from the operation room input device 29d (shown in FIG. 2), operate the X-ray detector 27 and the high voltage supply device 28, which are shown in FIG. 2, according to the instruction via the controller 4, and perform fluoroscopy or imaging. The imaging controlling 62 has functions that control the X-ray image generator 52 and the X-ray image processor 53 to generate and store the X-ray image, and display the X-ray image on the operation room display 29a, the X-ray image including at least one of the fluoroscopic image (the moving image) and the simple image (the still image such as the DA image).

The reproduction triggering 63 has functions that trigger a reproduction of the X-ray image stored in the X-ray image storage 54, and trigger displaying on the operation room display 29a, according to the instruction input from the operation room input device 29d (shown in FIG. 2).

The identifying 64 has a function that identifies a state of the X-ray diagnostic apparatus 1 on the basis of at least one of the holding device 2, the bed device 3, the X-ray irradiator 26 of the holding device 2, the X-ray detector 27 of the holding device 2, and the operation room display 29a, the state being any of steps included in a manipulation such as IVR (interventional radiology).

Figure 4:
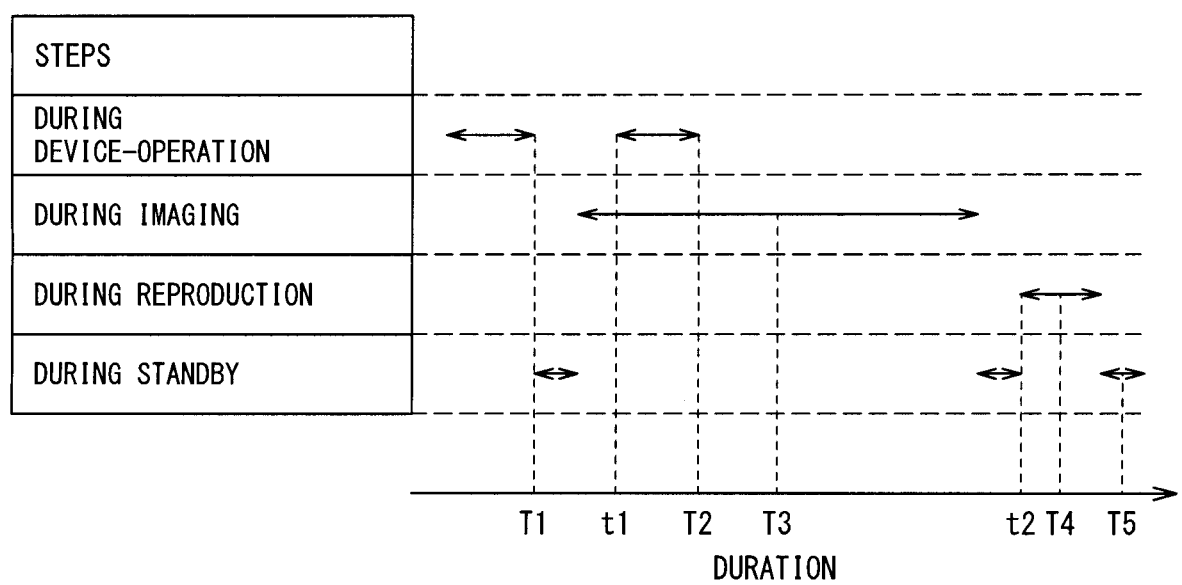
FIG. 4 is a diagram showing an example of time-series variation in steps included in a manipulation at the X-ray diagnostic apparatus according to the present embodiment.

FIG. 4 is a diagram showing an example of time-series variation in the steps included in the manipulation at the X-ray diagnostic apparatus 1 according to the present embodiment.

As shown in FIG. 4, the X-ray diagnostic apparatus 1 includes steps roughly classified into a step "during device-operation" after triggering of the operation of the holding device 2 or the bed device 3 by the device triggering 61, a step "during imaging" indicating during the imaging such as the fluoroscopy imaging and the simple imaging by the imaging controlling 62, a step "during reproduction" after triggering the reproduction of the X-ray image by the reproduction triggering 63, and a step "during standby" that does not fall into any of the above three steps. At least two of the steps "during device-operation", "during imaging" and "during reproduction" may be sometimes performed in parallel.

Returning back to FIG. 3, the operation detail determining 65 has a function of determining the operation detail of at least one of the holding device 2, the bed device 3, the operation room display 29a, and the speaker 29b, on the basis of the combination of the step included in the manipulation identified by the identifying 64 and a gesture of the manipulator recognized by the motion sensor 29c.

FIG. 5 is a diagram showing an example of the operation details by the combination of the step included in the manipulation and the gesture in the X-ray diagnostic apparatus 1 according to the present embodiment.

FIG. 5 shows the step included in the manipulation shown in FIG. 4. The step "during device-operation", which is one of the steps included in the manipulation shown in FIG. 5, includes step elements "during holding device-operation" and "during bed device-operation". The operation of the holding device 2 is triggered by the device triggering 61 (shown in FIG. 3) according to the input via the operation room input device 29d (shown in FIG. 2). The identifying 64 (shown in FIG. 3) identifies that the state is the step element "during holding device-operation" included in the step "during device-operation". In this case, when the motion sensor 29c (shown in FIGS. 2 and 3) recognizes any of gestures of left, right, upward and downward movements of a hand of the manipulator, the operation detail determining 65 (shown in FIG. 3) determines that the operation detail is stop of the operation of the holding device 2 (times T1 and T2 in FIG. 4).

The operation of the bed device 3 is triggered by the device triggering 61 (shown in FIG. 3) according to the input through the operation room input device 29d (shown in FIG. 2). The identifying 64 (shown in FIG. 3) identifies that the state is the step element "during bed device-operation" included in the step "during device-operation". In this case, when the motion sensor 29c (shown in FIGS. 2 and 3) recognizes any of gestures of the left, right, upward and downward movements of a hand of the manipulator, the operation detail determining 65 (shown in FIG. 3) determines that the operation detail is stop of operation of the bed device 3 (the times T1 and T2 in FIG. 4).

The step "during imaging", which is one of the steps included in the manipulation shown in FIG. 5, includes step elements "during simple fluoroscopy imaging-operation", "during LIH (last image hold)-display" and "during RM (road map)-operation" in the fluoroscopic imaging. When the identifying 64 (shown in FIG. 3) identifies that the state is the step element "during simple fluoroscopy imaging-operation" included in the step "during imaging", and when the motion sensor 29c (shown in FIGS. 2 and 3) recognizes any of gestures of left and right movements of a hand of the manipulator, the operation detail determining 65 (shown in FIG. 3) determines that the operation detail is turning on/off of an RM-operation in the fluoroscopic imaging on the operation room display 29a (time T3 in FIG. 4). On the other hand, when the motion sensor 29c (shown in FIGS. 2 and 3) recognizes any of gestures of upward and downward movements of a hand of the manipulator, the operation detail determining 65 (shown in FIG. 3) determines that the operation detail is change in an imaging program on the operation room display 29a (to a Next/Previous program) (the time T3 in FIG. 4).

When the identifying 64 (shown in FIG. 3) identifies that the state is the step element "during LIH-display" included in the step "during imaging", and when the motion sensor 29c (shown in FIGS. 2 and 3) recognizes any of gestures of left and right movements of a hand of the manipulator, the operation detail determining 65 (shown in FIG. 3) determines that the operation detail is change in brightness of the operation room display 29a (UP/DOWN) (the time T3 in FIG. 4). On the other hand, when the motion sensor 29c (shown in FIGS. 2 and 3) recognizes any of gestures of upward and downward movements of a hand of the manipulator, the operation detail determining 65 (shown in FIG. 3) determines that the operation detail is change in contrast of the operation room display 29a (UP/DOWN) (the time T3 in FIG. 4).

When the identifying 64 (shown in FIG. 3) identifies that the state is the step element "during RM-operation" in the fluoroscopic imaging included in the step "during imaging", and when the motion sensor 29c (shown in FIGS. 2 and 3) recognizes any of gestures of left and right movements of a hand of the manipulator, the operation detail determining 65 (shown in FIG. 3) determines that the operation detail is change in superposition coefficient of the X-ray image on the operation room display 29a (UP/DOWN) (the time T3 in FIG. 4). On the other hand, when the motion sensor 29c (shown in FIGS. 2 and 3) recognizes any of gestures of upward and downward movements of a hand of the manipulator, the operation detail determining 65 (shown in FIG. 3) determines that the operation detail is change to a fluoroscopic subtraction or the RM-operating in the fluoroscopic imaging on the operation room display 29a (the time T3 in FIG. 4). In the case of the fluoroscopic subtraction, the superposition coefficient between the mask image and the contrast image is "1 (100%)". A mask image of 100% is thus subtracted from the contrast image, thereby allowing only a contrast-imaged vascular image to be displayed. On the other hand, in the case of the RM-operation, the superposition coefficient is "less than 1". Thus, the background with low concentration (bone etc.) and a contrast-imaged vascular image are displayed.

Alternatively, when the identifying 64 (shown in FIG. 3) identifies that the state is the step "during imaging", and when the motion sensor 29c (shown in FIGS. 2 and 3) recognizes any of gestures of left and right movements of a hand of the manipulator, the operation detail determining 65 (shown in FIG. 3) determines that the operation detail is change in luminance of a room light (not shown) in the operation room (UP/DOWN). In this case, recognition of any of gestures of upward and downward movements of a hand of the manipulator by the motion sensor 29c (shown in FIGS. 2 and 3) allows the operation detail determining 65 (shown in FIG. 3) to determine that the operation detail is power on/off of the room light (not shown). Alternatively, when the identifying 64 (shown in FIG. 3) identifies that the state is the step "during imaging", and when the motion sensor 29c (shown in FIGS. 2 and 3) recognizes any of gestures of left, right, upward and downward movements of a hand of the manipulator, the operation detail determining 65 (shown in FIG. 3) determines that the operation detail is stop of X-ray irradiation by the X-ray irradiator 26.

The step "during reproduction", which is one of the steps included in the manipulation shown in FIG. 5, includes step elements "during moving image-reproduction", "during map image-display", "during still image-display", and "during DSA (digital subtraction angiography) image-display". When the identifying 64 (shown in FIG. 3) identifies that the state is the step element "during moving image-reproduction" included in the step "during reproduction", and when the motion sensor 29c (shown in FIGS. 2 and 3) recognizes any of gestures of left and right movements of a hand of the manipulator, the operation detail determining 65 (shown in FIG. 3) determines that the operation detail is change in a reproduction speed of the moving image on the operation room display 29a (UP/DOWN) (time T4 in FIG. 4). On the other hand, when the motion sensor 29c (shown in FIGS. 2 and 3) recognizes any of gestures of upward and downward movements of a hand of the manipulator, the operation detail determining 65 (shown in FIG. 3) determines that the operation detail is cut feeding forward or backward of a moving image on the operation room display 29a (the time T4 in FIG. 4).

When the identifying 64 (shown in FIG. 3) identifies that the state is the step element "during map image-display" included in the step "during reproduction", and when the motion sensor 29c (shown in FIGS. 2 and 3) recognizes any of gestures of left and right movements of a hand of the manipulator, the operation detail determining 65 (shown in FIG. 3) determines that the operation detail is execution of automatic angle function of the holding device 2 (reproduction of the X-ray irradiation angle) (the time T4 in FIG. 4). On the other hand, when the motion sensor 29c (shown in FIGS. 2 and 3) recognizes any of gestures of upward and downward movements of a hand of the manipulator, the operation detail determining 65 (shown in FIG. 3) determines that the operation detail is execution of an original image display function for a map image on the operation room display 29a (display of the original moving image) (the time T4 in FIG. 4).

When the identifying 64 (shown in FIG. 3) identifies that the state is the step element "during still image-display" included in the step "during reproduction", and when the motion sensor 29c (shown in FIGS. 2 and 3) recognizes any of gestures of left and right movements of a hand of the manipulator, the operation detail determining 65 (shown in FIG. 3) determines that the operation detail is panning of a still image on the operation room display 29a (the time T4 in FIG. 4). On the other hand, when the motion sensor 29c (shown in FIGS. 2 and 3) recognizes any of gestures of upward and downward movements of a hand of the manipulator, the operation detail determining 65 (shown in FIG. 3) determines that the operation detail is cut feeding forward and backward of the still image on the operation room display 29a (the time T4 in FIG. 4).

When the identifying 64 (shown in FIG. 3) identifies that the state is the step element "during DSA image-display" included in the step "during reproduction", and when the motion sensor 29c (shown in FIGS. 2 and 3) recognizes any of gestures of left, right, upward and downward movements of a hand of the manipulator, the operation detail determining 65 (shown in FIG. 3) determines that the operation detail is left, right, upward or downward pixel shift of a mask image (or a contrast image) for a DSA image on the operation room display 29a (the time T4 in FIG. 4).

When the identifying 64 (shown in FIG. 3) determines that the state is the step "during standby", and when the motion sensor 29c (shown in FIGS. 2 and 3) recognizes any of gestures of left and right movements of a hand of the manipulator, the operation detail determining 65 (shown in FIG. 3) determines that the operation detail is change in volume of the speaker 29b (UP/DOWN) (time T5 in FIG. 4). On the other hand, when the motion sensor 29c (shown in FIGS. 2 and 3) recognizes any of gestures of upward and downward movements of a hand of the manipulator, the operation detail determining 65 (shown in FIG. 3) determines that the operation detail is turn on/off of the speaker 29b (the time T5 in FIG. 4).

In each step (or step element) identified by the identifying 64, information that indicates operation details corresponding to respective various gestures may be displayed on the operation room display 29a. The manipulator can perform a gesture for operating the holding device 2 and the like while viewing information displayed on the operation room display 29a.

Returning back to FIG. 3, the operation controlling 66 has a function of operating at least one of the holding device 2, the bed device 3, the operation room display 29a and the speaker 29b according to the operation detail for at least one of the holding device 2, the bed device 3, the operation room display 29a and the speaker 29b, which has been determined by the operation detail determining 65.

For example, when the identifying 64 identifies that the state is the step element "during holding device-operation" included in the step "during device-operation", and when the motion sensor 29c (shown in FIGS. 2 and 3) recognizes any of gestures of left and right movements of a hand, the operation detail determining 65 determines that an operation of stop operating the holding device in operation is performed as shown in FIG. 5, and the operation controlling 66 stops the holding device 2 in operation. For example, when the identifying 64 identifies that the state is the step element "during simple fluoroscopy imaging-operation", and when the motion sensor 29c (shown in FIGS. 2 and 3) recognizes any of gestures of a left movement of a hand, the operation detail determining 65 determines that an operation of turning on the RM-operation in the fluoroscopic imaging is performed as shown in FIG. 5, and the operation controlling 66 turns on the RM-operation on the operation room display 29a.

The example of starting determination of the operation detail according to the step (or the step element) at the time of starting the step has been thus described. However, the embodiment is not limited to this case.

For example, when the identifying 64 identifies the step, the operation detail determining 65 starts determination of the operation detail according to the step at the time of recognizing a recognition start gesture. Referring to FIG. 4, the operation detail determining 65 starts determination of the operation detail according to the step "during reproduction", at the time of recognizing a hand raising gesture after a time t2.

Thus, the determination of the operation detail according to the step is started at the time of recognizing the recognition start gesture. Consequently, operation errors are avoided. The errors include operations of the device such as holding device 2 by movement of a person other than the manipulator in the field of view L and by movement by the manipulator who does not intend to operate the device.

Priority orders may be preset to the plurality of steps included in the manipulation to be determined. In a time period during which the steps included in the manipulation are overlap with each other, the operation detail determining 65 determines the operation detail corresponding to the gesture with the highest priority according to the priority order. In this case, determination is switched to that for the operation detail according to the step at the time of starting the step with a high priority order.

For example, when the step determined by the identifying 64 includes a first step having a high priority order and a second step started before the first step and having a low priority order, the operation detail determining 65 switches the determination of the operation detail according to the second step to the determination of the operation detail according to the first step at the time of starting the first step. Referring to FIG. 4, at a time t1, the operation detail determining 65 switches the determination of the operation detail according to the step "during imaging", which is the second step, to the determination of the operation detail according to the step "during device-operation", which is the first step.

The example has thus been described where in the case of preliminarily setting the priority orders to the plurality of steps, the determination of the operation detail according to the second step previously started and having the low priority order is switched to the determination of the operation detail according to the first step having the high priority at the time when the first step is started during the second step. However, the embodiment is not limited to this case.

For example, if the step determined by the identifying 64 includes the first step having the high priority order and the second step started before the start of the first step and having the low priority order, the operation detail determining 65 switches the determination of the operation detail according to the second step to the determination of the operation detail according to the first step at the time when a prescribed gesture (shown in FIG. 5) continuing before the start of the first step is finished (discontinuance for at least a prescribed time). Referring to FIG. 4, at the time when, after the time t1, continuation of the gesture of left or right movement of a hand before start of the step "during device-operation", which is the first step, is finished, the operation detail determining 65 switches the determination of the operation detail according to the step "during imaging", which is the second step, to the determination of the operation detail according to the step "during device-operation", which is the first step.

Thus, even if the first step having the high priority order is started during the second step previously started and having the low priority order, determination of the operation detail according to the second step is continued during continuation of the prescribed gesture. Consequently, an operation error can be avoided where if the first step is started during continuation of the prescribed gesture in the second step and the operations of the first step and the second step are in parallel, the device related to the first step is erroneously operated.

For example, if the step determined by the identifying 64 includes the first step having the high priority order and the second step started before the start of the first step and having the low priority order, the operation detail determining 65 switches the determination of the operation detail according to the second step to the determination of the operation detail according to the first step at the time of recognizing the recognition start gesture. Referring to FIG. 4, at the time of recognizing the hand raising gesture after the time t1, the operation detail determining 65 switches the determination of the operation detail according to the step "during imaging", which is the second step, to the determination of the operation detail according to the step "during device-operation", which is the first step.

Thus, even if the first step having the high priority is started during the second step previously started and having the low priority order, determination of the operation detail according to the second step is continued until the recognition start gesture is recognized. Consequently, an operation error can be avoided where if the first step is started during continuation of the prescribed gesture (shown in FIG. 5) in the second step and the operations of the first step and the second step are in parallel, the device related to the first step is erroneously operated.

The X-ray diagnostic apparatus 1 according to the present embodiment can identify the state (step or step element) included in the manipulation) of the X-ray diagnostic apparatus 1, and determine the operation detail on the basis of the combination of the gesture of the manipulator, such as a medical doctor, and the state of the X-ray diagnostic apparatus 1. Consequently, the treatment efficiency can be improved. Furthermore, unnecessary radiation exposure on the object S due to inefficient treatment can be reduced.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
   a display;
   a holding device including an X-ray irradiator, an X-ray detector, and a supporter that supports the X-ray irradiator and the X-ray detector;
   a bed device available to place an object on;
   a gesture detecting device configured to recognize a gesture of a person; and
   processing circuitry configured to identify a current step out of steps included in a manipulation, based on at least one of the display, the X-ray irradiator, the X-ray detector, the holding device, and the bed device, determine an operation detail based on a combination of the identified step and the recognized gesture, and operate at least one of the display, the holding device, the bed device, a speaker and a room light according to the determined operation detail.

2. The X-ray diagnostic apparatus according to claim 1 wherein
the processing circuitry is configured to identify a step of a reproduction of a moving image based on the display, to identify a step of an operation of the holding device based on the holding device, to identify a step of an operation of the bed device based on the bed device, or to identify a step of an imaging based on the X-ray irradiator and the X-ray detector.

3. The X-ray diagnostic apparatus according to claim 1, wherein
the processing circuitry is configured to start, when the step is identified, the operation detail according to the identified step in a time when recognizing a recognition start gesture as the gesture.

4. The X-ray diagnostic apparatus according to claim 1, wherein
when the steps are preset, priority orders are assigned to the respective steps in advance, and, in a time period while the steps overlap with each other, the processing circuitry is configured to identify a step with a highest priority according to the priority order.

5. The X-ray diagnostic apparatus according to claim 4, wherein
in a time when a first step with a high priority order, and a second step started before start of the first step and with a low priority order overlap, the processing circuitry is configured to switch the operation detail according to the second step to determination of the operation detail according to the first step at a time when continuation of the gesture before the start of the first step is finished.

6. The X-ray diagnostic apparatus according to claim 4, wherein
in a time when a first step with a high priority order, and a second step started before start of the first step and with a low priority order overlap, the processing circuitry is configured to switch the operation detail according to the second step to determination of the operation detail according to the first step at a time of recognizing a recognition start gesture as the gesture.

7. The X-ray diagnostic apparatus according to claim 1, wherein
the processing circuitry is configured to display information indicating a relationship between the gesture and the operation detail on a display.

8. The X-ray diagnostic apparatus according to claim 1, wherein the processing circuitry is configured to:
receive an instruction input from an input device;
trigger the holding device according to the instruction;
determine a step of an operation of the holding device after triggering the holding device; and
identify a gesture during the operation of the holding device as an operation of stopping an operation of the holding device.

9. The X-ray diagnostic apparatus according to claim wherein the processing circuitry is configured to:
receive an instruction input from an input device;
trigger the bed device according to the instruction;
identify a step of an operation of the bed device after triggering the bed device; and
determine a gesture during the operation of the bed device as an operation of stopping an operation of the bed device.

10. The X-ray diagnostic apparatus according to claim 1, wherein the processing circuitry is configured to:
identify a step of a fluoroscopy imaging after start of the fluoroscopy imaging; and
determine a gesture during the fluoroscopy imaging as at least one of operations of turning on/off an RM (road map)-operation in the fluoroscopic imaging and change in an imaging program.

11. The X-ray diagnostic apparatus according to claim 1, wherein the processing circuitry is configured to:
identify a step of a fluoroscopy imaging after start of the fluoroscopy imaging; and
determine a gesture during the fluoroscopy imaging as an operation of stop of X-ray irradiation from the X-ray irradiator.

12. The X-ray diagnostic apparatus according to c wherein
the processing circuitry is configured to:
receive an instruction input from an input device;
trigger a reproduction of a moving image according to the instruction;
identify a step of the reproduction after the reproduction of the moving image; and
determine a gesture during the reproduction as an operation of stopping an operation of the reproduction of the moving image.

13. The X-ray diagnostic apparatus according to claim 2, wherein the processing circuitry is configured to:
identify a step of a standby, when neither a step of the reproduction of the moving image, a step of the operation of the holding device, a step of the operation of the bed device, nor a step of the imaging is applicable; and
determine a gesture during the standby as at least one of an operation of changing a volume of a speaker and turning on/off the speaker.

14. The X-ray diagnostic apparatus according to claim 1, wherein the gesture detecting device is configured to capture the person to recognize the gesture of the person.

15. The X-ray diagnostic apparatus according to claim 1, wherein each of the steps included in the manipulation has a session.

* * * * *